(12) United States Patent
Huckle

(10) Patent No.: US 6,297,286 B1
(45) Date of Patent: Oct. 2, 2001

(54) THERAPEUTIC USE AND FORMULATION

(75) Inventor: Richard Michael Huckle, Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/708,813

(22) Filed: Nov. 8, 2000

(30) Foreign Application Priority Data

Nov. 9, 1999 (GB) .................................... 9926528
Jun. 9, 2000 (GB) .................................... 0014191

(51) Int. Cl.$^7$ .................................... A01N 33/02
(52) U.S. Cl. .................... 514/646; 514/282; 514/284; 424/649
(58) Field of Search .................... 514/646, 282, 514/284; 424/649

(56) References Cited

U.S. PATENT DOCUMENTS

| | | | |
|---|---|---|---|
| 5,468,744 | * 11/1995 | Raffa et al. | 514/282 |
| 5,733,936 | * 3/1998 | Buschmann et al. | 514/646 |
| 5,919,826 | * 7/1999 | Caruso | 514/629 |
| 6,056,968 | * 5/2000 | Gilbert et al. | 424/422 |
| 6,221,394 | * 4/2001 | Gilbert et al. | 424/473 |

FOREIGN PATENT DOCUMENTS

| | | |
|---|---|---|
| 9840053 | 3/1998 | (WO) . |
| 0032558 | 12/1999 | (WO) . |

OTHER PUBLICATIONS

Barnung, S.K., M. Treschow, F.M. Borgbjerg (1997) "Respiratory depression following oral tramadol in a patient with impaired renal function" *Pain* 71:111–112.

Grond, Stefan, Thomas Meuser, Detlev Zech et al. (Sep., 1995) "Analgesic efficacy and safety of tramadol enantiomers in comparison with the racemate: a randomised, double–blind study with gynaecological patients using intravenous patient–controlled analgesia" *Pain* 62(3):313–320.

Shipton, E.A. (2000) "Reviews: Tramadol—Present and Future" *Anaesth Intensive Care* 28:363–374.

* cited by examiner

*Primary Examiner*—James H. Reamer
(74) *Attorney, Agent, or Firm*—Saliwanchik, Lloyd & Saliwanchik

(57) ABSTRACT

Substantially single-enantiomer(−)-tramadol, and its metabolites and structural and/or functional analogues, are useful for the prevention and/or treatment of one or more symptoms selected from nausea, vomiting, dizziness, blurred vision, drowsiness, somnolence, hallucinations, respiratory depression, constipation and euphoria. In particular, substantially single enantiomer (−)-tramadol, and its o-desmethyl metabolite, have been found to be potent antiemetics.

20 Claims, 4 Drawing Sheets

THERAPEUTIC USE AND FORMULATION

FIELD OF THE INVENTION

This invention relates to new therapeutic uses of tramadol and its structural and/or functional analogues, and to new formulations thereof.

BACKGROUND OF THE INVENTION

Tramadol has the chemical name (+/−)-trans (RR,SS)-2-[(di-methylamino)methyl]-1-(3-methoxyphenyl) cyclohexanol, and which is generally, and erroneously, referred to in literature as the cis(RS,SR) diastereomer, is a centrally acting, binary analgesic that is neither opiate-derived, nor is a non-steroidal, anti-inflammatory drug (NSAID). It is used to control moderate pain in chronic pain settings, such as osteoarthritis and postoperative cases, and acute pain, such as dental pain.

Used in therapy as a racemic mixture, the (+)-enantiomer binds to the $\mu$-opioid receptor, and both enantiomers inhibit 5-hydroxytryptamine (serotonin) and noradrenaline (norepinephrine) reuptake. Tramadol's major active metabolite, O-desmethyltramadol (M1), shows higher affinity for the $\mu$-opioid receptor and has at least twice the analgesic potency of the parent drug.

Despite the fact that tramadol is chemically unrelated to the opioids adverse side-effects associated with administration of tramadol are similar to those of the opioids.

The efficacy and safety of racemic tramadol and its separate enantiomers have been the subject of much study. It has been observed that the (+)-enantiomer has significantly higher analgesic potency than the (−)-enantiomer. It has also been observed that side-effects such as nausea and vomiting are more frequently experienced on administration of the (+)-enantiomer than the (−)-enantiomer. However, the conclusion drawn from these observations, taking into account efficacy and safety, has been to continue use of the racemate; see Pain 1995 September; 62(3):313–20 and Anaesthetist 1998 May; 47(5):387–94.

SUMMARY OF THE INVENTION

Surprisingly, we have now found that not only are the side-effects caused by administration of (−)-tramadol less severe than those caused by the racemate or (+)-enantiomer, but also that prophylactic or therapeutic administration of (−)-tramadol can prevent or diminish those side-effects and other symptoms typically associated with administration of opioid drugs, or similar symptoms caused by other means. This effect is believed not to be limited to (−)-tramadol, but to extend to the metabolites of (−)-tramadol and to structural and/or functional analogues of (−)-tramadol. By the latter we mean any drug known to operate pharmacologically in a similar manner to (−)-tramadol.

Thus, according to a first aspect of the invention substantially single enantiomer (−)-tramadol, or a metabolite or a structural and/or functional analogue thereof, is used in the manufacture of a medicament for the prevention and/or treatment of one or more symptoms selected from nausea, vomiting, drowsiness, somnolence, dizziness, respiratory depression, blurred vision, hallucinations, constipation and euphoria, or other central nervous system (CNS) side-effects, especially nausea and/or vomiting. In fact, substantially single enantiomer (−)-tramadol is new class of anti-emetic drug which as a broad spectrum of activity like no other currently marketed anti-emetic.

The symptoms to be alleviated may be associated with administration of another drug. Thus, according to a further aspect of the invention, substantially single enantiomer (−)-tramadol, or a metabolite or a structural and/or functional analogue thereof, is formulated with said another drug as a combined preparation (kit) for simultaneous, separate or sequential use, in the treatment or prevention of a condition for which the said another drug is administered.

DETAILED DESCRIPTION OF THE INVENTION

Examples of drugs of the type which may be used to alleviate the above-mentioned symptoms include substantially single enantiomer (−)-tramadol and its structural and functional analogues including aryl cyclohexanol derivatives such as venlafaxine, codeine, pethidine, dextromethorphan and pentazocine, and derivatives thereof. The metabolites of (−)-tramadol are also believed to be of use in the present invention, and such metabolites are described in detail by Shipton, Anaesth. Intensive Care (2000) 28:363–374, which is incorporated herein by way of reference. In the following, unless otherwise stated, reference to substantially single enantiomer (−)-tramadol is intended to embrace the metabolites and analogues of that compound.

While the surprising effects upon which the present invention is based may be common to a number of different compounds, substantially single enantiomer (−)-tramadol and substantially single enantiomer (−)-O-desmethyltramadol are the preferred compounds use in the present invention, with substantially single enantiomer (−)-tramadol being the most preferred.

In the context of this Application, by substantially single enantiomer we mean that one enantiomer is present in an enantiomer excess of at least about 70%, preferably at least about 80%, more preferably at least about 90%, and most preferably at least about 95%. Although it will be understood that any form of tramadol which contains sufficient (−)-tramadol may achieve the beneficial results of the present invention.

The symptoms to be alleviated may be caused by a number of different stimuli. For instance, the symptoms may be caused by administration of any of a number of drugs from different groups. Non-limiting examples of these include:

1) Antidepressants, e.g. moclobemide, trazadone, 1-tryptophan, paroxitine, protryptyline, nefazodone, fluvoxamine.

2) Anxiolytics, e.g. buspirone.

3) Antipsychotics, e.g. clozapine, chlorpromazine.

4) Anticonvulsants, e.g. lamotrigine, gabapentin, carbamezepine.

5) Drugs used in the treatment of neurodegenerative disease, such as muscarinic, nicotinic and dopamine agonists typically used in the treatment of Alzheimer's disease and Parkinson's disease. Specific examples include donepezil, interferon, apomorphine, pergolide, levodopa, bromocriptine, amantadine, tolcapone, selegiline.

6) CNS stimulants, e.g. dexamphetamine, methylphenidate.

7) Drugs used in the treatment of migraine, e.g. ergotamine, methysergide, naratriptan, zolmitriptan.

8) Drugs involved in modulating monoamine or opioid activity, e.g. imipramine, reserpine, venlafaxine, lithium salts, citalopram, fluoxetine, morphine.

9) Opioid drugs, e.g. fentanyl, morphine, sufentanil, diamorphine, buprenorphine, dextromoramide, methadone, oxycodone, phenacozine, nefopam, codeine.

10) Alkaloids, such as those used to treat cancer, e.g. cisplatin.

11) Other drugs useful in cancer treatment or therapy.

It is recognised that there may be overlap between some of the above drug groups.

It is generally preferred to administer substantially single enantiomer (−)-tramadol as a protective, prophylactic dose, which becomes effective prior to release into the body of the drug responsible for the undesirable symptoms. It is believed that substantially single enantiomer (−)-tramadol may be administered at least two to three hours prior to the drug responsible for the undesirable symptoms, and still be effective in preventing and/or treating those symptoms. For these purposes it is convenient to formulate a dosage form in which the (−)-tramadol tramadol is provided in immediate release form and the other drug is provided in controlled release form. This is readily achieved using current technology. Under certain circumstances however it may be preferred to administer the drug responsible for causing the undesirable symptoms before the (−)-tramadol, or at a substantially faster release rate, or at a substantially slower release rate. Any of the dosage forms described in WO-A-9840053 would be suitable for use in the present invention, optionally with any of the formulations described in WO-A-0032558.

Alternatively, the symptoms are not side-effects associated with drug administration, but instead symptoms of a particular condition, e.g. migraine, morning sickness, motion sickness, post-operative nausea and vomiting (PONV), or cancer.

Irrespective of the cause of the symptoms, the present invention is thought to be particularly useful in preventing and/or treating nausea and/or vomiting.

The invention is especially useful for preventing and/or treating nausea and/or vomiting caused by administration of an analgesic drug, in particular an opioid agonist, such as any of the opioid drugs. Morphine, fentanyl and codeine are especially prone to causing emesis. The dual benefits of anti-emesis and additive or synergistic analgesia can be obtained in circumstances where substantially single enantiomer (−)-tramadol, or an analgesic metabolite structural and/or functional analogue thereof, is formulated as a combined product (kit) for simultaneous separate or sequential use with an emetic opioid agonist.

The invention is also useful in preventing and/or treating nausea and/or vomiting caused by administration of tramadol, in racemic or non-racemic form, including substantially single enantiomer (+)-tramadol and non-racemic mixtures enriched in that enantiomer. In this case, optimal results are achieved by administration of (−)-tramadol before, or at a faster rate than, the other form of tramadol containing the (+)-enantiomer. Although, benefits may also be achieved by simultaneous administration at the same rate, provided that sufficient (−)-tramadol is administered to achieve the desired result. Usually the nausea and/or vomiting will be caused by an analgesic drug other than tramadol.

Patients who are particularly susceptible to the nausea caused by opioid drugs are those having abnormal liver cytochrome P4502D6 (sparteine oxygenase) activity. Extensive metabolizers of sparteine have O-demethylation activity which allows them to convert (+)-tramadol to (+)-M1, or codeine to morphine, and thereby experience rapid pain relief. Tramadol's major active metabolite, O-desmethyltramadol (M1), shows higher affinity for the $\mu$-opioid receptor and has at least twice the analgesic potency of the parent drug. In contrast, poor metabolizers of sparteine can easily be diagnosed as such by medical practitioners, for example by observing that codeine has no analgesic effect on them.

The CYP2D6 gene encoding sparteine oxygenase is highly polymorphic, and an ever-increasing number of mutations are being identified. The wild-type gene is CYP2D6*1A. Any person not having the wild-type gene can be categorised as exhibiting abnormal enzyme activity. The precise nature of any particular mutation determines the degree to which a patient exhibits abnormal enzyme activity. Thus, by applying simple laboratory genetic analysis techniques it is possible to ascertain the approximate rate at which (+)-tramadol will be metabolised by a particular patient, and therefore how rapid and effective analgesia will be.

In accordance with the present invention it is envisaged that patients phenotypically or genotypically diagnosed as extensive metabolizers of racemic tramadol will particularly benefit from administration of substantially single enantiomer (−)-tramadol, since they are especially prone to suffering from side-effects such as nausea and vomiting. Furthermore, the administration regime may be tailored to suit any individual patient once his or her CYP2D6 genotype is known.

One group of patients known to be susceptible to adverse tramadol-related side-effects is the elderly, who may not be able to clear the drug or its metabolites from their bodies as efficiently as younger people (Barnung SK et al, (1997) Pain 71:111–2). Respiratory depression upon dosing with centrally-acting analgesics (e.g. morphine and codiene) is not unusual in the elderly and others with impaired renal function. The invention may therefore be of used with these patient types to prevent or alleviate this.

The invention is also particularly useful in preventing and/or treating nausea and/or vomiting associated with the administration of apomorphine. Apomorphine is used in the treatment of Parkinson's disease, but one major side effect associated with its use is nausea, often accompanied by vomiting. Apomorphine-induced erections in patients suffering from Parkinson's disease are proving more common than originally thought. Thus, it is believed that apomorphine may have a possible role in the treatment of impotence. As it has now been found that substantially single enantiomer (−)-tramadol is a potent anti-emetic, its combined use with apomorphine not only provides an improved treatment for Parkinson's disease, but also an improved treatment for impotence for a wide range of patient types, both male and female.

Substantially single enantiomer (−)-tramadol may be used as the sole agent to prevent or alleviate the above-mentioned symptoms, or it may be used and/or formulated for use with another drug having similar or complementary activity.

For instance, substantially single (−)-tramadol may be used with other anti-emetics, e.g. 5-HT$_3$ receptor antagonists such as ondansetron and granisetron, antihistamines such as hydroxyzine and dimenhydrinate, anticholinergics such as scopolamine, benzamides such as metocloptramide, butyrophenones such as droperidol and haloperidol, phenothiazines such as chlorpromazine and prochlorperazine, and tachykinin NK-1 receptor antagonists.

Substantially single enantiomer (−)-tramadol may be formulated for use in the invention, whether with or without another drug, for administration by any of the conventional routes, for instance oral, rectal, transdermal, nasal, ophthalmic, pulmonary and injectable (subcutaneous and intravenous). Suitable dosage forms include tablets, suppositories, capsules, e.g. containing mutliparticulates, patches, polymer implants, aerosols, liposomes or microparticulates for injection, and any other conventional dosage form.

The amount of substantially single enantiomer (−)-tramadol to be used in the present invention depends upon the cause and severity of the symptoms to be prevented and/or treated, and the patient type. Generally, where substantially single enantiomer (−)-tramadol is used to prevent nausea and/or vomiting associated with another drug, a suitable dosage amount lies in the range 20 and 400 mg, preferably 20 to 300 mg, although amounts lying outside these ranges may also prove to be useful.

Patients that may benefit from the present invention include humans and other mammals.

Substantially single enantiomer (−)-tramadol may be prepared by any of the techniques reported in the literature, for instance as described in our co-pending Application WO-A-0032554.

The effects upon which the present invention are based are reported in the following Examples.

EXAMPLE 1

Assessment of Nausea

Tramadol and its pure enantiomers were examined for their nauseous effects in the ferret. For comparative purposes the effects of the active metabolite of (+)-tramadol ((+)-T), (+)-O-desmethyltramadol ((+)-ODT), were also tested. Orally-dosed ferrets were observed over a period of 4 hours for signs of retching and vomiting. Any ferret that retched or vomited over the 4 hour period was regarded as a responder, i.e. as exhibiting nausea.

The results are given in the graph in FIG. 1. As expected, (+)-ODT is highly emetic. (−)-tramadol ((−)-T) is seen to be non-emetic at doses of up to 200 mg/kg. In comparison, (+)-tramadol ((+)-T) induces nausea in 75% of ferrets at 50 mg/kg, while the racemate causes nausea in 25% of animals at 100 mg/kg. Although the racemate ((+/−)-T) is a 50:50 mixture of the two enantiomers it is seen to induce less nausea than would be expected based on its content of (+)-enantiomer. This disparity can be explained by the ability of the (−)-enantiomer to modulate emesis, i.e. to act as an anti-emetic.

Bioanalysis of plasma samples and liver microsome analysis have shown that tramadol is metabolised similarly in the ferret and the human. It is therefore expected that the results obtained can be extrapolated to humans, suggesting that (−)-tramadol may be useful generally as an anti-emetic, and particularly in combination with racemic or (+)-enantiomeric tramadol.

EXAMPLE 2

Ability of (−)-Tramadol to Modify the Emetic Action of Pro-emetic Drugs 50 mg/kg of (−)-tramadol was orally administered to ferrets 180 minutes prior to administration to the same ferrets of one of the following pro-emetic drugs:

i) apomorphine, 0.125 mg/kg subcutaneously ii) ipecacuhana, 1.25 mg/kg orally iii) morphine, 0.125 mg/kg subcutaneously.

The ferrets were observed continuously, by recording on to videotape (for a period of 4 hours) and scored for numbers of retches (dry vomits), vomits, and the time of onset. The results obtained are shown in FIGS. 2 to 4, expressed as percentage change from ferrets which, prior to administration of the pro-emetic, had been treated with vehicle alone, as a control. Each of FIGS. 2 to 4 shows error bars corresponding to standard errors.

FIG. 2 shows the results obtained in relation to apomorphine-induced emesis. As can be seen, (−)-tramadol inhibits the emetic effect of apomorphine with an effective dose for 50% reduction in emesis ($ED_{50}$) of greater than 3 mg/kg but less than 10 mg/kg.

EXAMPLE 3

Ability of (−)-Tramadol to Modify Cisplatin-Induced Emesis

Cisplatin is a platinum-derived cytotoxic agent commonly used in the treatment of cancer. Cisplatin is one of the most highly emetic therapeutics used in the clinic today. Emesis observed with this agent can be divided into two phases, acute (day 1) where emesis is mainly driven by 5-HT derived mechanisms, and delayed (days 2 and 3) where emesis is driven by mechanisms other than 5-HT.

(−)-tramadol was administered orally to ferrets every 8 hours (i.e. 3 daily doses) for 3 days at 50 mg/kg prior to administration of cisplatin (5 mg/kg), intraperitoneal administration). The animals were observed (recorded on videotape continuously for a period of 3 days and scored for numbers of retches and vomits and the time of onset.

The test was repeated using the following different dosage regimes for (−)-tramadol: 3 mg/kg orally twice daily, and 10 mg/kg orally twice daily.

Figure 1:
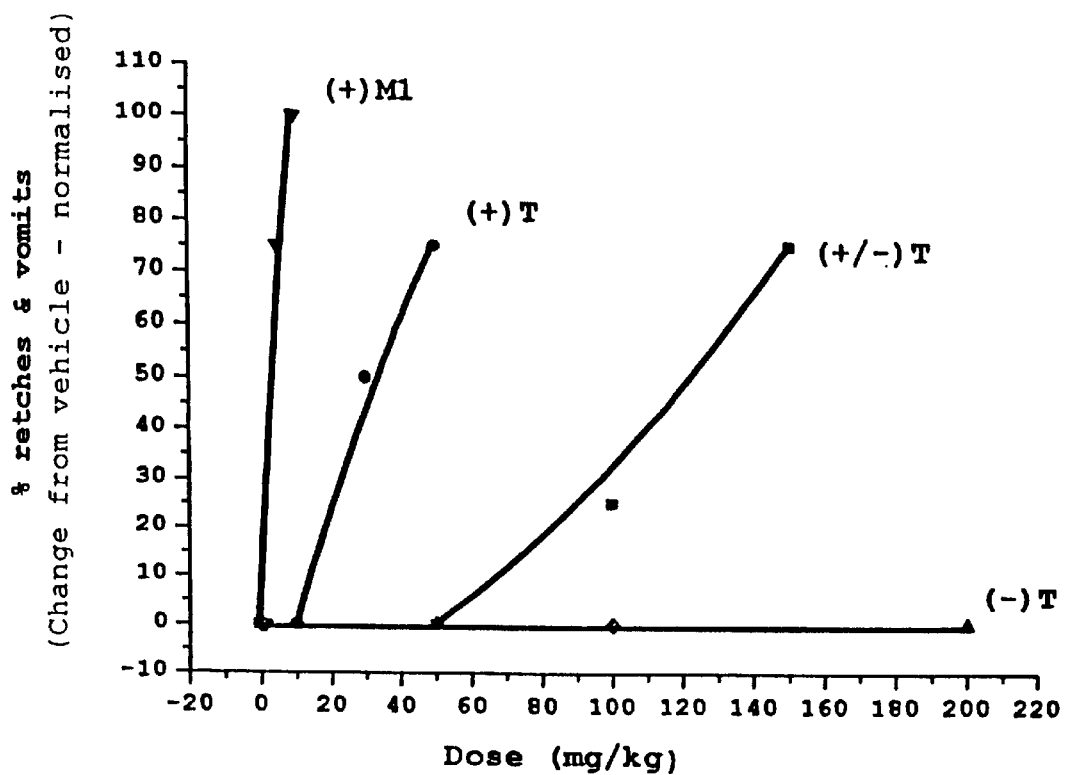
Figure 2:
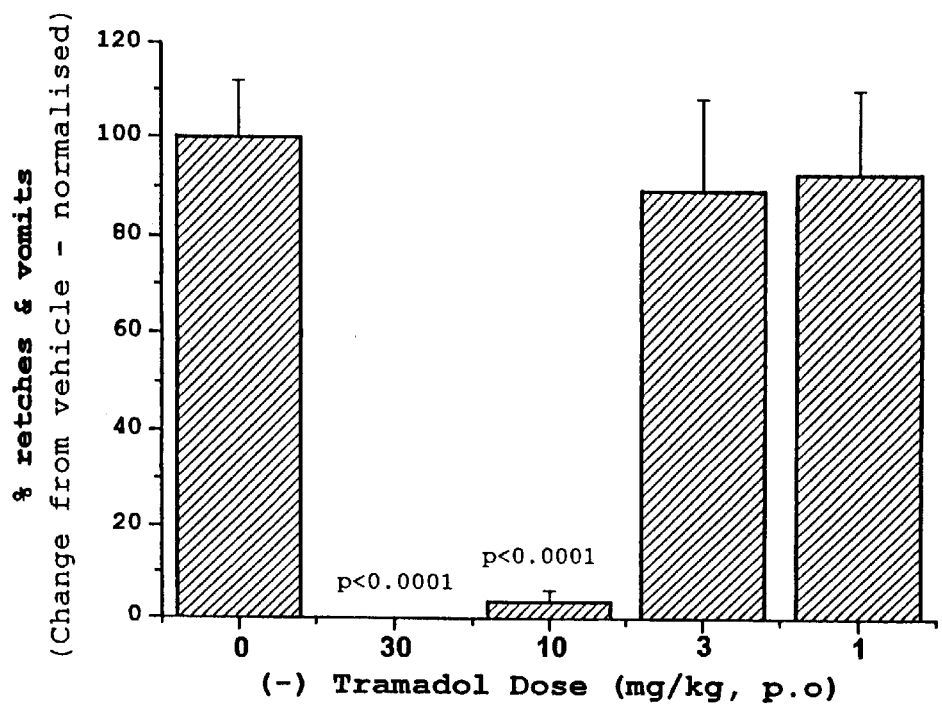
Figure 3:
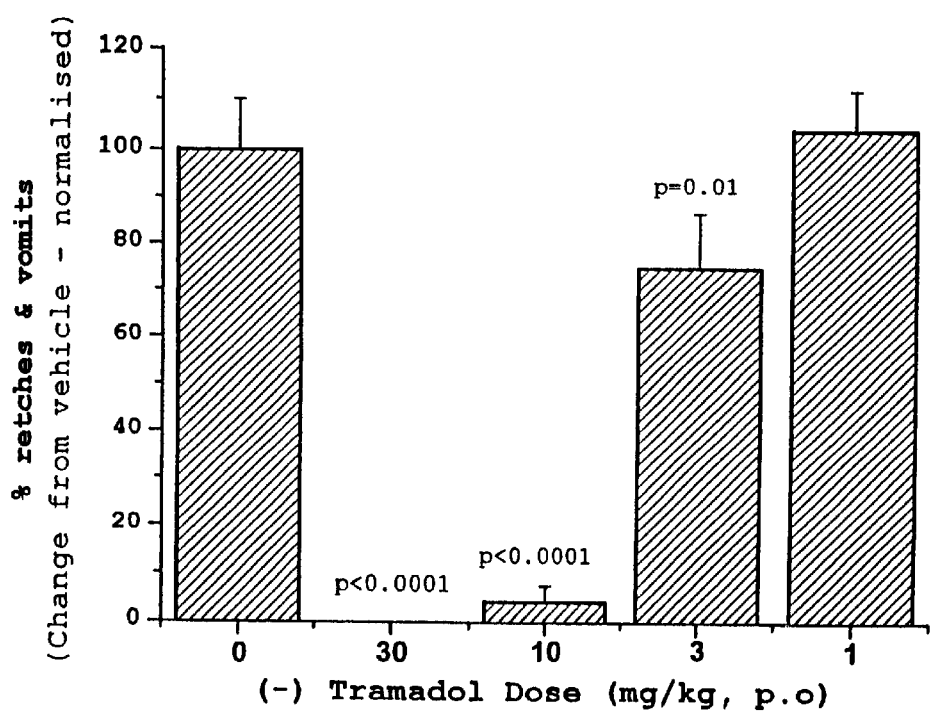
FIG. 3 shows the results obtained in relation to ipecacuhana-induced emesis. As can be seen, (−)-tramadol inhibits the emetic effect of ipecacuhana with an $ED_{50}$ of greater than 3 mg/kg but less than 10 mg/kg.
Figure 4:
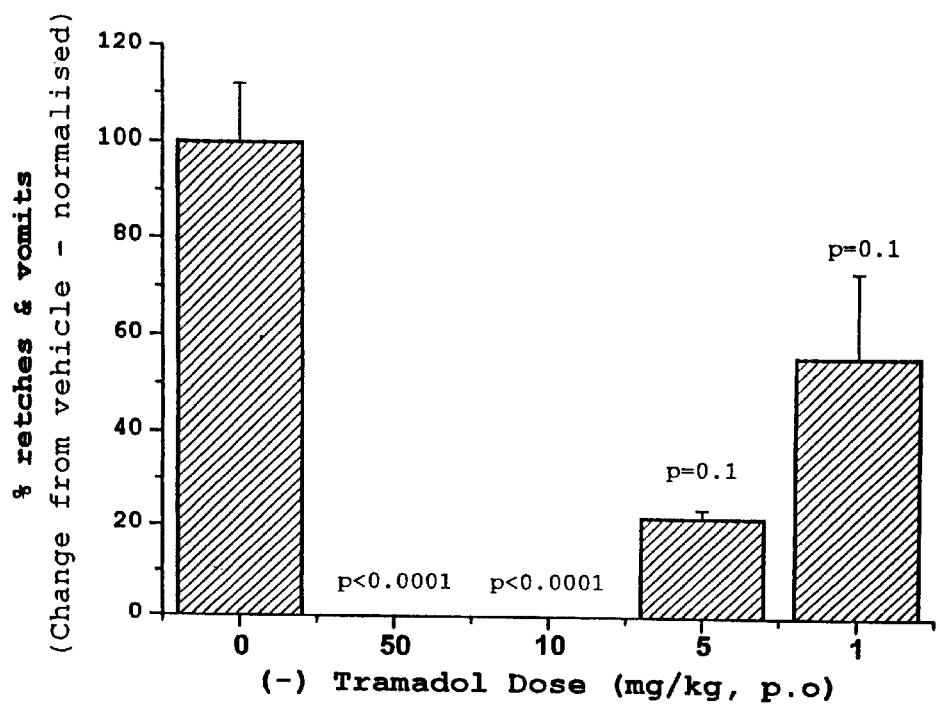
FIG. 4 shows the results obtained in relation to morphine-induced emesis. As can be seen, (−)-tramadol inhibits the emetic effect of morphine with an $ED_{50}$ of greater than 1 mg/kg but less than 5 mg/kg.
Figure 5:
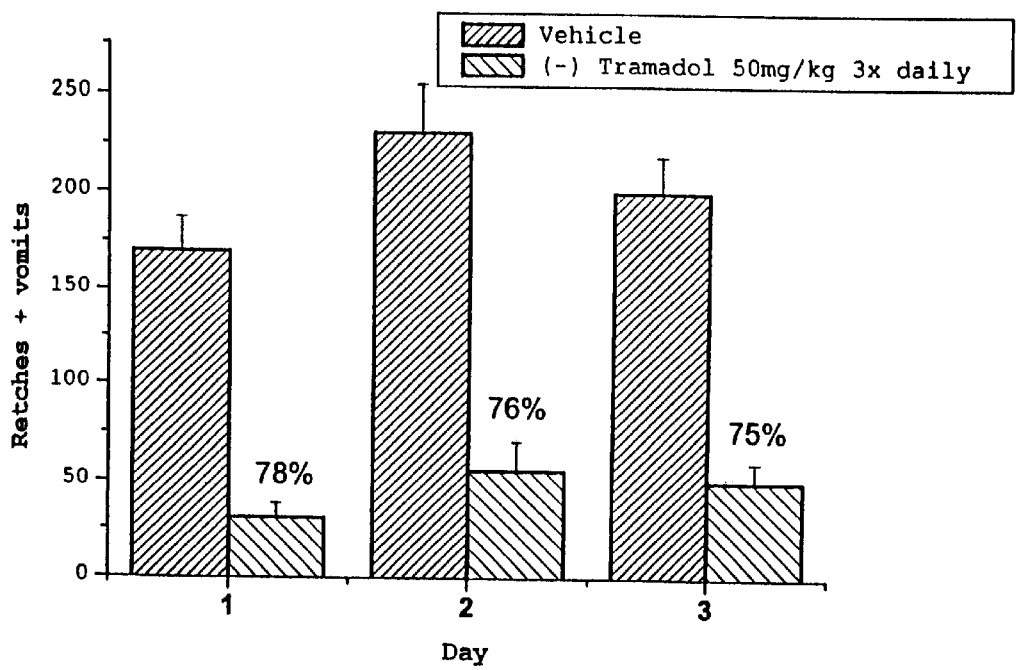
Figure 6:
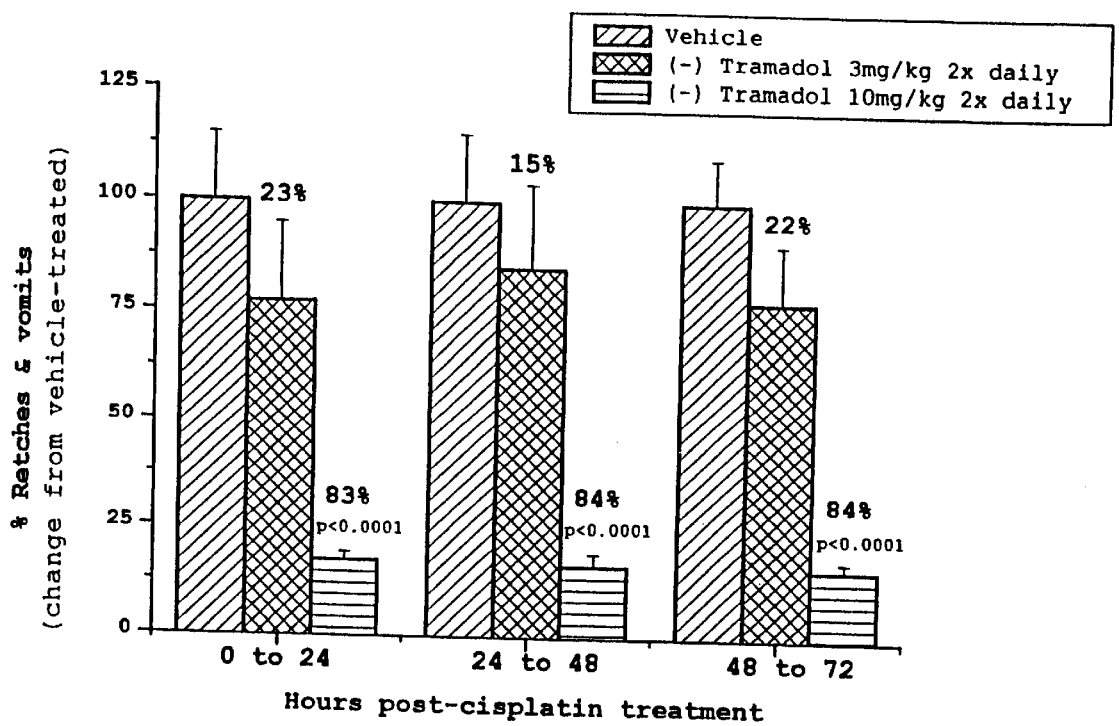

The results are presented in FIGS. 5 and 6. FIG. 5 shows the number of retches and vomits observed in animals to which vehicle rather than (−)-tramadol was administered, as compared to animals to which (−)-tramadol was administered. FIG. 6 presents its results in the same way as FIGS. 2 to 4, as a percent change from vehicle-treated animals.

The results show that (−)-tramadol inhibits the emetic effect of cisplatin in both the acute and delayed phases, with an $ED_{50}$ of greater than 3 mg/kg but less than 10 mg/kg.

The results reported in Examples 2 and 3 illustrate the breadth of activity of (−)-tramadol as an anti-emetic.

In contrast, it has been found that, at clinically-relevant doses, ondansetron is ineffective in inhibiting the emetic effect of apomorphine and morphine, and also ineffective against the delayed phases of cisplatin-induced emesis.

Allometrically scaling the values of $ED_{50}$ of (−)-tramadol obtained in the ferret to man, suggests that a dosage between 27 and 271 mg (−)-tramadol will be effective in controlling nausea and vomiting caused by the above pro-emetic drugs.

I claim:

1. A method for the prevention and/or treatment of one or more symptoms selected from the group consisting of nausea, vomiting, dizziness, blurred vision, drowsiness, somnolence, hallucinations, respiratory depression, constipation and euphoria, wherein said method comprises administering to a patient substantially single enantiomer (−)-tramadol, or a metabolite, or structural or functional analogue thereof.

2. The method, according to claim 1, wherein the symptom or symptoms include nausea and/or vomiting.

3. The method, according to claim 1, wherein the symptom or symptoms are associated with administration of a drug.

4. The method, according to claim 3, wherein the drug is selected from the group consisting of analgesics, antidepressants, anxiolytics, anticonvulsants, drugs used to treat neurodegenerative dieases, CNS stimulants, drugs used in the treatment of migraine, drugs involved in modulating monoamine or opioid activity, alkaloid drugs, and drugs used in cancer treatment or therapy.

5. The method, according to claim 4, wherein the drug is racemic tramadol or non-racemic tramadol, including substantially single enantiomer (+)-tramadol.

6. The method, according to claim 4, wherein the drug is an opioid drug.

7. The method, according to claim 4, wherein the drug is a $\mu$-opioid agonist.

8. The method, according to claim 4, wherein the drug is morphine.

9. The method, according to claim 4, wherein the drug is apomorphine.

10. The method, according to claim 4, wherein the drug is cisplatin.

11. The method, according to claim 4, wherein the drug is for administration to a patient exhibiting abnormal CYP2D6 liver enzyme activity.

12. The method, according to claim 1, wherein the symptom or symptoms are associated with a condition selected from the group consisting of migraine, morning sickness, motion sickness, post-operation nausea and vomiting (PONV), and cancer.

13. The method, according to claim 1, comprising administration of substantially single enantiomer (−)-o-desmethyltramadol.

14. A product comprising substantially single enantiomer (−)-tramadol, or a metabolite, or a structural or functional analogue thereof, and another drug having a side-effect selected from the group consisting of nausea, vomiting, dizziness, blurred vision, drowsiness, somnolence, hallucinations, respiratory depression, constipation and euphoria, as a combined preparation for simultaneous, separate or sequential use for treating a condition for which the said another drug is administered.

15. The product, according to claim 14, wherein the said another drug is is selected from the group consisting of analgesics, antidepressants, anxiolytics, anticonvulsants, drugs used to treat neurodegenerative diseases, CNS stimulants, drugs used in the treatment of migraine, drugs involved in modulating monoamine or opioid activity, alkaloid drugs, and drugs used in cancer treatment or therapy with the proviso that if the said another drug is tramadol the product does not contain a 50:50 weight ratio of (+):(−)-tramadol.

16. The product, according to claim 14, wherein the said another drug is an analgesic drug, and the product is for providing analegia, with the proviso that if the said another drug is tramadol the product does not contain a 50:50 weight ratio of (+):(−)-tramadol.

17. A product comprising substantially single enantiomer (−)-tramadol, or a metabolite, or a structural or functional analogue thereof, and another anti-emetic drug, as a combined preparation for simultaneous, separate or sequential use, for preventing and/or treating nausea and/or vomiting.

18. The product, according to claim 14, wherein the substantially single enantiomer (−)-tramadol, metabolite, or analogue thereof, is in immediate release form and the said another drug is in controlled release form.

19. The product, according to claim 14, wherein the substantially single enantiomer (−)-tramadol, metabolite, or analogue thereof, is in controlled release form and the said another drug is in immediate release form.

20. A product comprising substantially single enantiomer (−)-tramadol, or a metabolite, or structural or functional analogue thereof, and apomorphine as a combined preparation for a simultaneous, separate or sequential use, for the treatment of sexual impotence.

* * * * *